(12) United States Patent
Rojas et al.

(10) Patent No.: US 6,786,082 B2
(45) Date of Patent: Sep. 7, 2004

(54) SYSTEM FOR A NON-INVASIVE ONLINE CONTINUOUS MEASUREMENT OF PHASE LEVELS IN CONVERTERS OR PYROMETALLURGICAL FURNACES

(76) Inventors: Luis Paredes Rojas, ½ Oriente 1050, Oficina 204, Viña del Mar (CL); Alfredo Zolezzi Garreton, ½ Oriente 1050, Oficina 204, Viña del Mar (CL)

( * ) Notice: Subject to any disclaimer, the term of this patent is extended or adjusted under 35 U.S.C. 154(b) by 0 days.

(21) Appl. No.: 10/145,538

(22) Filed: May 13, 2002

(65) Prior Publication Data

US 2003/0209078 A1 Nov. 13, 2003

(51) Int. Cl.$^7$ .......................... G01N 29/18; C21D 11/00
(52) U.S. Cl. ...................... 73/61.45; 73/290 V; 73/627; 266/94
(58) Field of Search ................ 73/61.45, 590, 73/290 V, 627; 266/94

(56) References Cited

U.S. PATENT DOCUMENTS

| | | | |
|---|---|---|---|
| 3,720,351 A | 3/1973 | Coulter et al. | 222/1 |
| 4,213,404 A | 7/1980 | Spaulding | 110/229 |
| 4,320,659 A * | 3/1982 | Lynnworth et al. | 73/589 |
| 4,368,877 A * | 1/1983 | Baumert | 266/99 |
| 4,477,279 A | 10/1984 | Nauman | 75/382 |
| 5,803,948 A * | 9/1998 | Sizov et al. | 75/556 |
| 5,836,192 A * | 11/1998 | Getman et al. | 73/290 V |
| 6,234,023 B1 * | 5/2001 | Collins et al. | 73/597 |
| 6,298,008 B1 * | 10/2001 | Lyon et al. | 367/99 |
| 6,324,911 B1 * | 12/2001 | Scarffe | 73/627 |
| 6,397,656 B1 * | 6/2002 | Yamaguchi et al. | 73/1.82 |
| 6,594,596 B1 * | 7/2003 | Rojas et al. | 702/72 |

FOREIGN PATENT DOCUMENTS

| | | |
|---|---|---|
| GB | 2083182 A | 3/1982 |
| JP | 09071806 A | 3/1997 |

* cited by examiner

*Primary Examiner*—Hezron Williams
*Assistant Examiner*—John Hanley
(74) *Attorney, Agent, or Firm*—Greenberg Traurig, LLP; Charles Berman, Esq.

(57) ABSTRACT

A non-invasive online system for continuous measurements of phase levels in a converter or pyrometallurgical furnace in smelting and conversion processes, consisting in a electrical signal generator, transducers that convert said electrical signals in mechanical waves placed on the outer end of air blowing tuyeres, coupling means between said system and the shell of the converter, transducers placed in the direction of the axis orthogonal to the phases plane for applying mechanical waves that travel in a transversal direction into the converter, a mechanical waves sensor placed around the external wall of the shell of the converter that receives the reflected signal, a crystal local oscillator, means for the preamplification of the signal, an analogous/digital interface, a means for data acquisition, a means for processing the signals so as to determine the power of the reflected signal and the propagation time of the signal between the moment it is emitted by the transducer and the moment in which the reflected signals are received by the sensor, a memory means to store the continuous values of the phase levels and a visualization means for displaying the continuous values of the phase levels.

17 Claims, 10 Drawing Sheets

FIGURE 1
(Previous State of the Art)

FIGURE 2
(Previous State of the Art)

Discrete Measurement of Phase Levels Measurement Scheme

Figure 11

Continuous measurements of phase levels Measurement Scheme

SYSTEM FOR A NON-INVASIVE ONLINE CONTINUOUS MEASUREMENT OF PHASE LEVELS IN CONVERTERS OR PYROMETALLURGICAL FURNACES

FIELD OF APPLICATION

Present invention is related to the mining area, particularly to the pyrometallurgic area, specifically to the smelting and conversion process that occurs in furnaces and converters for production of refined metals when applying a field of mechanical waves in their interior.

PREVIOUS STATE OF THE ART

Within the mining processes, for example copper, a Converter, the Teniente Converter, used as the sole primary fusion system, has a system allowing injection of dry concentrate through injecting tuyeres, thereby turning it into an autonomous system. The Teniente Converter is the smelter's most important furnace since it defines its operational cycles. Once the equipment's operational conditions have been defined regarding concentrate composition, the fusion capacity and kinetics of the process depend on flow and oxygen enrichment of air blown through tuyeres.

The Teniente Converter (basically a horizontal cylinder with an outer mantle or shell lined in its interior with refractory material of determinate thickness within which 125020 C. chemical reactions occur, with dry concentrate injecting tuyeres, air blowing tuyeres and a drainage system placed at a certain height over ends of the Converter) is fed with a copper concentrate of approximately 28% copper content, injecting additionally through blowing tuyeres oxygen enriched air that produce a series of reactions that increase copper concentrate until it reaches 75% copper content.

The Teniente Converter operation is based on heat generated by pyritical decomposition and sulphur oxidisation reactions and consists mainly of melting the solid raw materials that are fed into it, oxidise part of the load and obtain as a product two liquid phases, one rich in copper (white metal, of higher density) and another formed basically by oxides present in the bath (slag, of lesser density which remains over the metallic bath or white metal). Additionally, gases rich in sulphur dioxide are generated during the operation, which are sent to the acid plant for treatment. The Teniente Converter delivers as a final product white metal, slag and gases.

The white metal in the Teniente Converter is a liquid solution comprised basically by a mixture of copper and iron sulphides ($Cu_2S$ and FeS) and contains additionally a part of the impurities present in the concentrates. Ellimination of these impurities occurs during the subsequent conversion processes.

White metal's higher density in relation to slag causes the white metal drops to descend through the bath to form a melted metal phase at the bottom of the furnace.

The melt's slag is formed by oxides fed to the converter; iron oxides produced by FeS oxidisation. Within the types considered the following are found: Fayalite ($2FeOSiO_2$), Magnetite ($Fe_3O_4$) Silica ($SiO_2$), Allumina ($Al_2O_3$), calcium oxides (CaO), copper oxides ($Cu_2O$) and White Metal ($Cu_2S$) trapped mechanically.

The desirable characteristics for slag are:

Should be miscible with the metal bath (white metal).

Low copper solubility.

Be fluid in order to minimise metal bath, concentrate and particle entrapment, and to allow adequate evacuation through the slag taphole.

The gas is formed basically by sulphur dioxide ($SO_2$), oxygen ($O_2$), Nitrogen ($N_2$) and water steam ($H_2O$).

Today, the process of obtaining white metal by Teniente Converter (CT) operation is subject to several problems whose solution has been attempted by different means. Amongst these difficulties we can mention the lack of online measurement of levels of the different phases. Currently, this measurement is carried out with a rod that is inserted into to the liquid metal thereby locating an operator over the converter, with the inherent risks involved by this technique. Furthermore, another main problem in CT operation is the formation of accretions at ends of air blowing tuyeres that inject oxygen enriched over the bath, since obstruction of airflow consequently decreases the chemical reactions within the converter, thereby decreasing its fusion capacity. Additionally, the accretions adhere firmly to the refractory material and part of this last is removed together with them, producing serious wear due to use of the tuyeres cleaning machine to eliminate the accretions, ultimately producing internal ruptures evidenced at short term by the leakage of material to the exterior.

Furthermore, the slag entraps mechanically as well as chemically, in approximately the same proportions, a significant copper content (around 8%). This copper must be recovered subsequently in a slag treatment furnace with the greater cost involved for the complete process.

In the white metal phase chemical reactions occur due to oxygen injection. These chemical reactions have their own kinetics given by the contact surface between the bubbles and fluid metal that corresponds to the interphase where the chemical reactions occur.

An increase in the chemical reactions means an increase in the production of desired metal in a fixed time period. This has its basis in kinetics, $v=ke^{-E/k^*T}$, where E is the activation energy. In this way, the emission of mechanical, for example sonic, waves speeds up a specific reaction, as it is able to supply a certain amount of energy (activation energy) and control it, meaning also that it is selective.

Specialized literature is aware of the fact that mechanical waves travel through solids as well as liquids and gases. Effectively, application of ultrasound in gases and metals in liquid state at high temperatures behaves like mechanical waves in general (See "Ultrasound Fundamentals" Jack Blitz, Alhambra Editorial, $1^{st}$ Spanish edition of 1969, pages 31–33).

Because of this, present invention employs mechanic wave transmission of certain characteristics to maximise the physical-chemical coupling of different media. Additionally, using the transmission and reflective properties of these mechanical waves that travel through different media (of different densities), it supplies an online and non-invasive invasive measurement of parameters very important for an optimal operation of the process.

BRIEF DESCRIPTION OF THE INVENTION

Present invention consists of a system for generating mechanical waves, sonic as well as ultrasonic, of specific characteristics, transmitted to the interior of a CT so as to maximise the physical-chemical coupling of different media. Additionally, using the transmission and reflective properties of these mechanical waves that travel through different media (of varying densities), it supplies an online and non invasive measurement of parameters that are very important for an optimal operation of a process.

So, a system has been implemented that increases the kinetics of chemical reactions and in consequence, an increase in the production of metal.

This higher production of metal results from the higher efficiency of oxygen reactions within the metal bath. The reaction capacity of oxygen per unit of volume of the metal bath per time unit in a converter or furnace is measured through the SBSR (Specific Bath Smelting Rate), and is theoretically defined by:

$$SBSR = e \cdot f \cdot Qo/V_{Bath}$$

Where: e=eficiency of oxygen consumption; f=oxygen enrichment; Qo=air flow; and $V_{Bath}$=bath volume.

The CT, under influence of the mechanical wave field (for example sonic, ultrasonic or infrasonic) that operates on the metal bath, slag and injected air improves its fusion cycle in terms of an increase in production of metal bath ($V_{Bath}$), in presence of the mechanical wave field.

Additionally there is a quicker homogenisation of the mixture, which stabilises the temperature as well as the density of the mixture, allowing it to approach thermal equilibrium. On the other hand the system eliminates the accretions that form at the ends of the air blowing tuyeres, permitting a relatively constant flow of air to the CT reacting with the higher density fluid, thus extending the operational time of the CT by avoiding the interruption of the process to eliminate said accretions through use of the tuyere cleaning machine that uses sharp tools to do the job.

As a result there is an increase in the useful life of the refractory as well as the CT.

Certainly, another result is the ellimination, to some extent, of the metal entrapped in the slag. The selective attack of the mechanical waves on the different components of the slag inhibits the entrapment of metal by it, thus reducing the quantity of copper trapped mechanically, because said waves deliver enough energy to make the metal drops decant, reducing it greatly.

Another aim of present invention is to provide continuous and discrete on line measurements of temperature and phase levels.

In all industrial processes, the stabilisation of variables is essential for achieving a good process control. In piromet-allurgical converters, a good control of the level of the white metal allows to decrease the copper loss due to drag by the slag and also avoids foaming.

Moreover, a good control of the level of slag avoids unnecessary heat loss. Meaning that if we subject converters that contain in their interior fluids of different densities to mechanical waves, these will have different propagation behaviours, and as it is known that their reflection coefficient depends on the media they are transmitted through, the phase levels and the refractory wear can be determined in real time or on line by relating these different reflection coefficients.

On line measurement of temperature of metal bath and slag and eventually of the temperature of the gaseous phase of the CT, allows a constant monitoring of the system, so as to take the corresponding action for a better use of the energy to increase fusion. Additionally it allows to avoid high fluctuations in temperature that produce thermal shock in the refractory. For this reason, the proposed measuring system submits the information directly to the Central Control System of the process in order to execute the programmed operations for each situation.

In the same way, the system detects the white metal and slag levels within certain discrete ranges.

BRIEF DESCRIPTION OF THE DRAWINGS

FIG. 3 corresponds to a first application of the invention to a transducer, set up to apply mechanical waves to travel longitudinally with the airflow.

FIG. 4 corresponds to a second application of the invention to a transducer set up to apply mechanical waves to travel transversally with the airflow.

FIG. 5 corresponds to a third application of the invention to a transducer set up to apply mechanical waves that propagate in a resonant chamber, so as to apply a large number of components of different amplitudes of said waves with the airflow.

DETAILED DESCRIPTION OF THE INVENTION

Present invention consists in a non-invasive system and method to apply mechanical waves directly to a metal fluid at temperatures of around 1250° C. Essentially it consists in a series of transducers that generate mechanical waves that travel to the fluid metal through the oxygen-injecting tuyeres of a converter or pirometallurgical furnace.

This system consists in a means to generate electrical signals (1), transducers, for conversion from electric to mechanic signals (5) and a mechanical connection (21) to ensure a perfect coupling with the mantle or shell (22) of the CT, through one of the blowing tuyeres (19) into which air is injected. (FIG.7)

Additionally it has an analogical/digital interface (27), sonic sensors (6) and a unit (26) for processing signals and acquiring data for the monitoring of important variables of the process.

Figure 1:
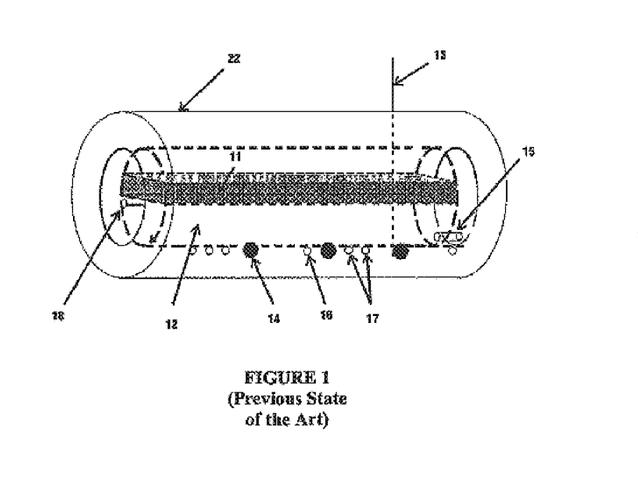
FIG. 1 shows the general schematic structure of a Pirometallurgical Converter, (Convertidor Teniente (Previous State of the Art)).
Figure 2:
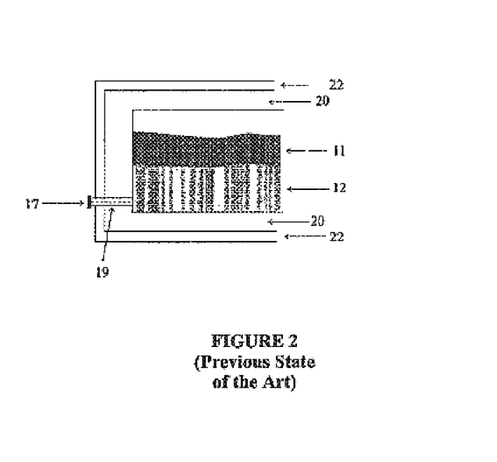
FIG. 2 shows a cross section of FIG. 1 (Previous State of the Art).
Figure 6:
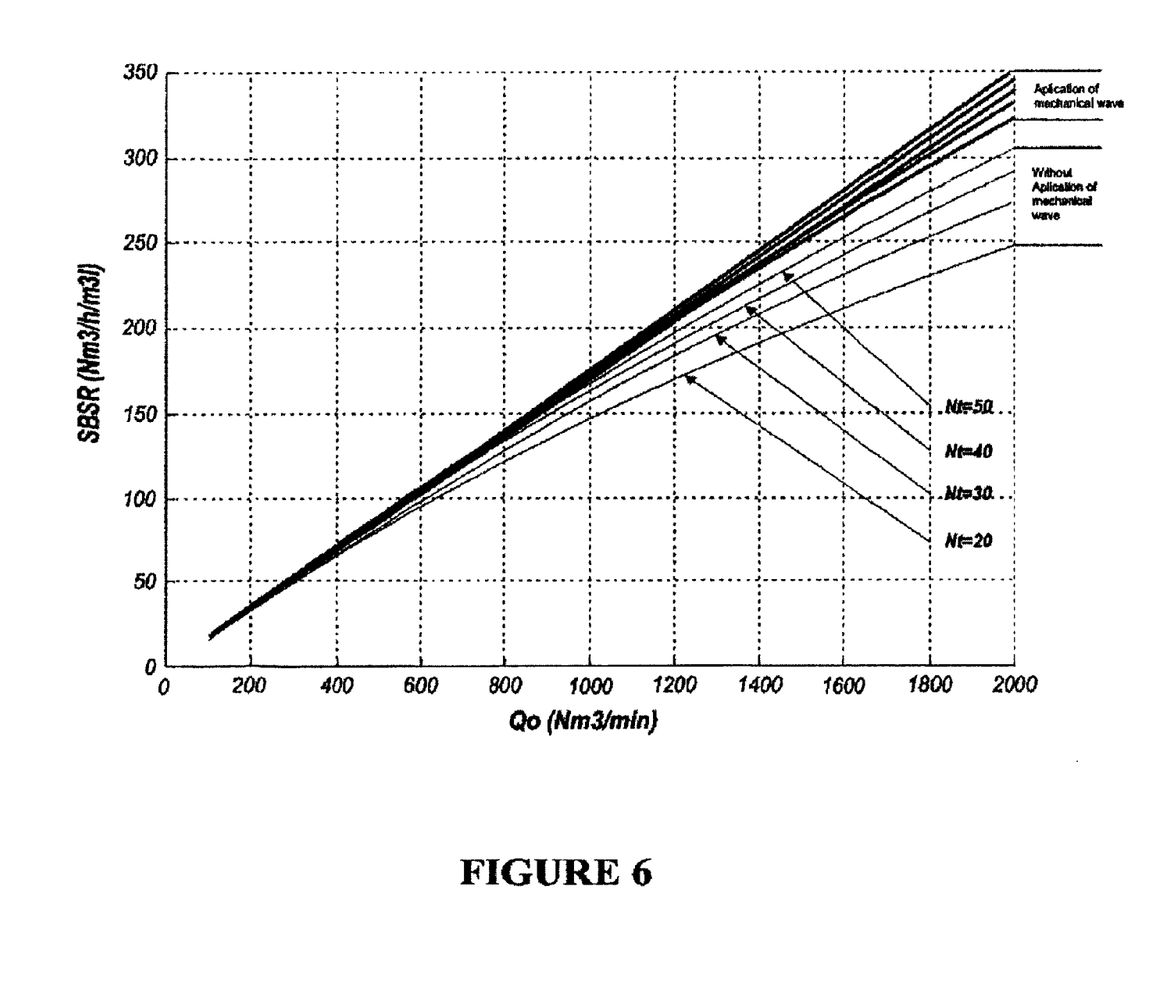
FIG. 6 is a graph of the SBSR (Specific Bath Smelting Rate) index, where the curves show this index with and without the application of aforementioned waves. The different curves are parametrised depending on the number of tuyeres that inject air into the metal bath.
Figure 7:
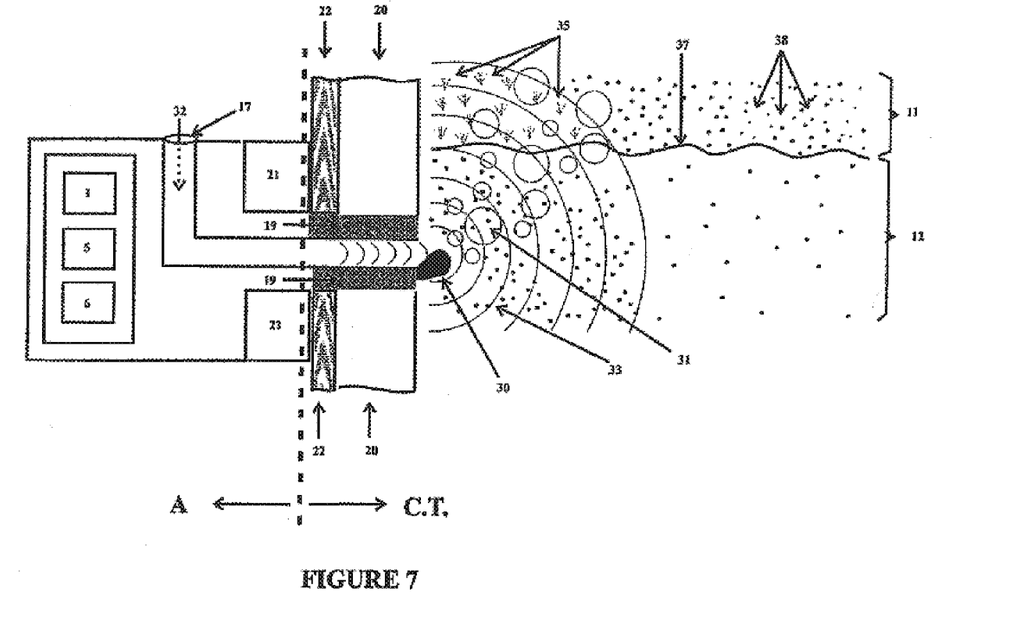
FIG. 7 shows the invention system applied to the CT, in a schematic form and cross section.

In FIG. 7 a schematic diagram shows the invention system (A) which has in its interior a layout of sonic transducers (5), set up to agree with the propagation direction and amplitudes of the mechanical waves (33) to be applied to the metal bath (12) and slag (11). The breaking or removal of accretions (30) can also be seen, as well as the detachment of copper from the slag (35), whereas in the sector to which the mechanical waves have not been applied, the copper trapped (38) in the slag has not been able to come loose.

In FIG. 3 a transducer is set up to apply mechanical waves in a longitudinal direction to the airflow is described. For this purpose the air blowing tuyere has been placed in a side duct to form an angle equal to or less than 90° (α) with the airflow entrance and the transducer, remaining this last linearly and directly at the height of the oxygen enriched air inciding in the metal bath. Thus the mechanical waves travel in a longitudianl directin with the airflow that reaches said metal bath.

FIG. 4 describes a second application of the transducer, set up to apply mechanical waves that travel transversally with the airflow. This last can be done with a straight tuyere in the direction of the entrance of the airflow, and this time at least one transducer is placed transversally to the air blowing tuyere (19). This ensures that the mechanical waves travel in a transversal direction with the airflow that reaches the metal bath.

FIG. 5 shows a third application of the invention, with a transducer within the resonant chamber which is part of the air blowing tuyere (19), forming a truncated cone attached to the shell of the CT in the truncated or narrowest end. In this way the transducer emits the mechanical waves which will resound first in the chamber, producing waves with a variety of components of different amplitudes that travel with the airflow to the interior of the CT.

The invention system (A) is coupled or joined to a pirometallurgical converter by one the blowing tuyeres (19) through a coupling piece (21) that ensures the mounting and a perfect seal between them. The coupling piece (21) adheres to the shell (22) of the CT by mechanical means. The shell is covered by refractory (29). The blowing tuyere (19) that injects air (32) enters the invention system and follows on into the interior of the tuyere (19) till it reaches the metal fluid (12). The waves (33) that come from the transducer (5) are transmitted through the air (32) that circulates through the tuyere (19) till it reaches the metal fluid (12) where it gets incorporated producing physical-chemical phenomena that allow to optimise the CT operation.

Another action developed by the invention, consists on preventing the formation of accretions in the blowing tuyeres and elliminating the wear of the refractory (29) resulting from the cleaning of said accretions. It is a well known fact that the highest refractory wear in the tuyeres area (19) of the CT is due to the chemical reactivity that occurs in head of the tuyere and to the effect of the sharp tools of the tuyeres cleaning machine that uses a mechanical attack to clean the accretions. Avoiding the formation of accretions means a sharp decrease in the wear of the refractory (29). The ellimination of the refactory (20) wear and decrease or ellimination of the mechanical attack of the tuyere cleaning machine avoids interrupting the process due to filtrations in the tuyeres.

Another result of the use of the invention is to lower the copper (38) entrapped by the slag (11). The selective attack of the mechanical waves (33) over the different components of slag (11) makes the copper detach (35) from the slag (11) at least in its mechanical aspect, as the application of these waves delivers enough energy to decant the white metal drops trapped in the slag and reduce the Cu2O avoiding losses, and minimizing subsequent treatment to the slag (11) to extract its copper content.

Discrete Measurement of Phase Levels for a Pyrometallurgical Converter

Figure 9:
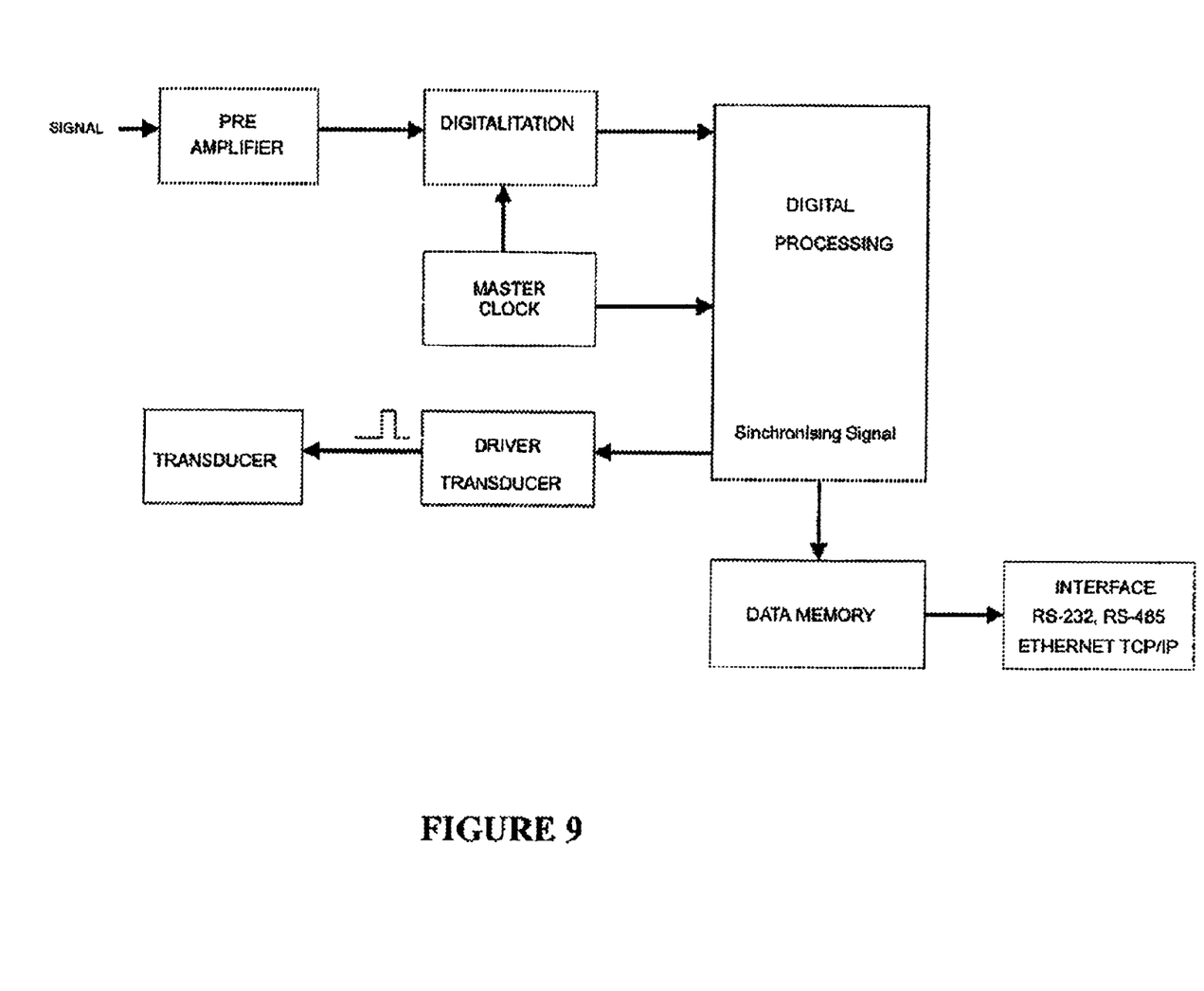
FIG. 9 shows a schematic figure of the circuit for the measurement of the time lapsed between the emission to the signal and reception of the different echos of the signal, while doing the discrete and continuous measurement of phase levels.
Figure 10:
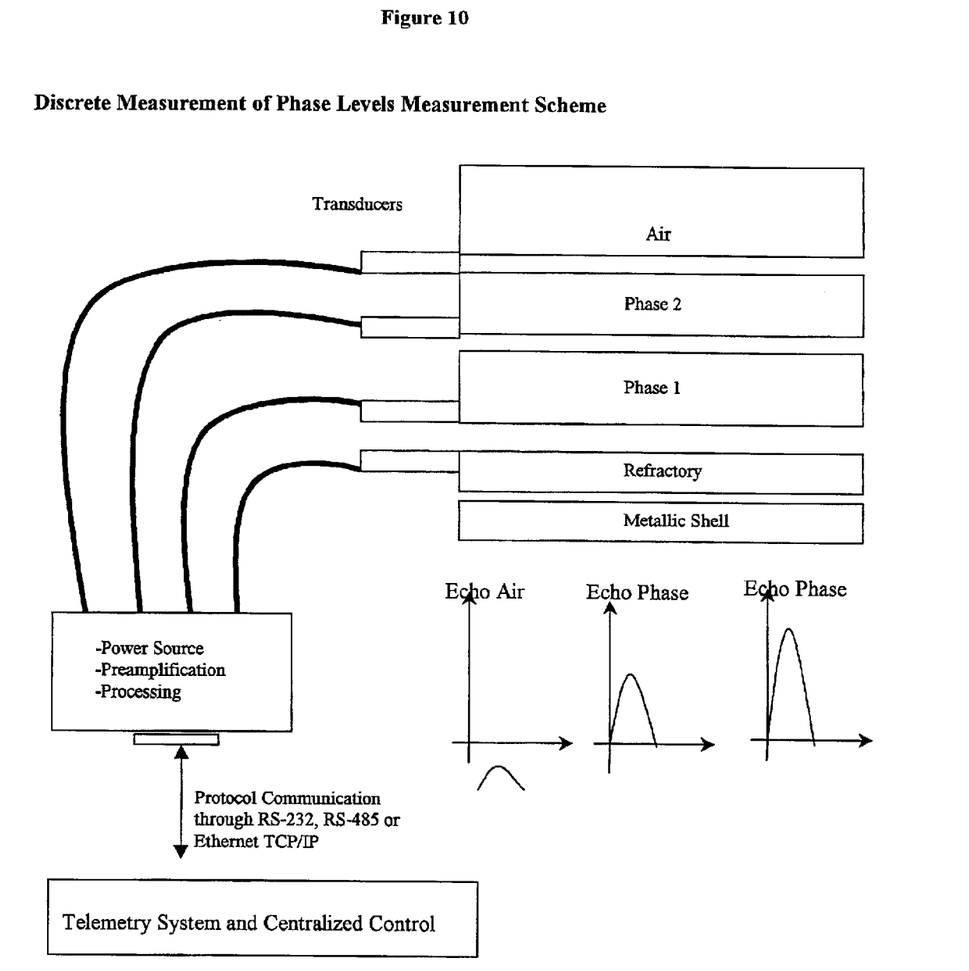
FIG. 10 is an example of a descrete measurement of the phase levels.

The measurement is based on the determination of the level of a reflected ultrasonic, sonic or infrasonic signal (echo pulses), in the limiting zone between the different existing phases present in the interior of the CT (from here on called interphases) needed to be maintained between certain levels during the operation. To do this measurement, an ultrasonic, sonic or infrasonic transducer (5) is used with the capacity to generate a signal of intermediate power and detect the reflected signal by at least one sensor (6), placed directly beside or integrated to, the transducer, or by one or more sensors placed around the shell of the CT. Considering the density difference between the phases (11, 12 and gases), the ultrasonic or sonic signal reflected by the different interphases will have a different level characteristic of each phase. The measurement of the amplitude of the reflected signal indicates the phase present in front of the transducer at that moment, delivering thereby a discrete measurement of the position of the interphase.

The resolution of this measurement is determined by the number of transducers and the distances between them, but for the purpose of having an alarm system that warns when the phase is at a certain level, only one transducer is needed.

An electronic circuit has been implemented capable of measuring the time lapsed between the echo pulses, which must be done in real time, integrated with the electronics that detect and preamplify the echoes.

The signal received is digitalised and processed by a DSP (Digital Signal Processor). The processor determines the amplitude of the signal and thereby determines the phase facing each transducer.

The position of the transducers is known so the information thus obtained allows to determine, in a discrete range, the position of the different interphases, o the alarm states defined (on the basis of the position of the transducers). These discrete levels and alarm state values are stored finally in a outgoing memory that can be read through a serial RS-232, RS-485 or Ethernet TCP/IP communication port, which are the most common communication standards of digital data in the industrial equipment field.

Another objective, in consequence, is to make available the measurement in the RS-232, RS-485 and TCP/IP communication standards and allow the incorporation of these values to the instrumentation network of the pirometallurgical converter, so they can be available in a Centralized Control System. This Centralized System must analyse the values obtained against the control references stored and execute the previously programmed actions (operating registries, levels of different alarms, etc)

Continuous measurement of Phase Levels for a Pirometallurgical Converter

Figure 11:
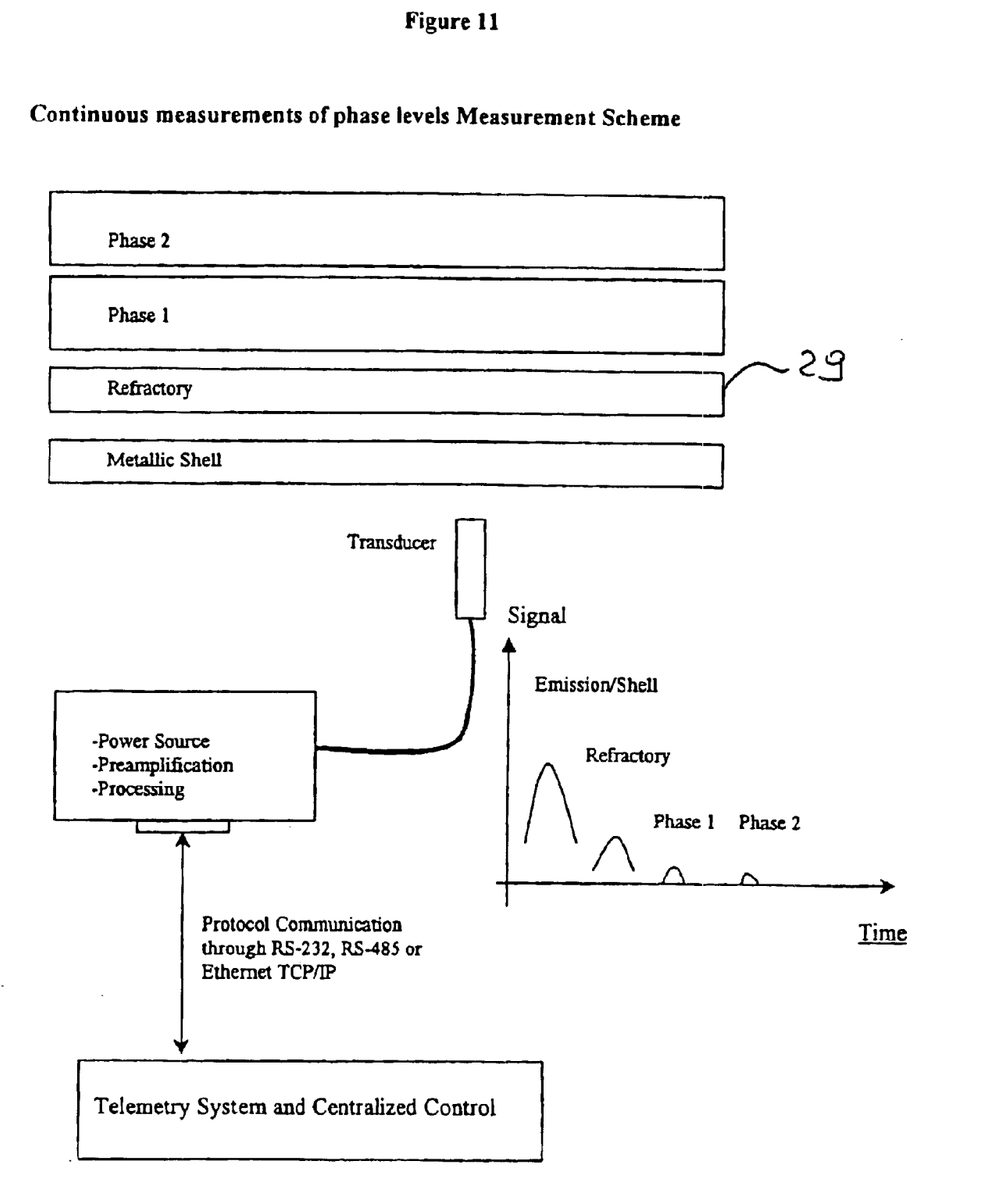
FIG. 11 is an example of a continuous measurement of the phase levels.

The measurement is based on determination of the time of propagation of a sonic, ultrasonic or infrasonic signal between the interphases that separate the different phases whose level must be known. To do this measurement a sonic, ultrasonic or infrasonic transducer (5) with capacity to generate an intermediate power signal and detect the reflected signal(echo pulses). Considering the density difference between the phases, the ultrasonic signal is reflected by the different interphases, returning a fraction of the power to the transducer that generated it. The measurement of the propagation time of the signal, between the moment in which it is emitted by the transducer and the moment in which the different echoes are received, considering a constant propagation speed, allows us to determine the position of the different interphases relative to the transducer.

An electronic circuit has been implemented capable of measuring the time lapsed between the echo pulses, which must be done in real time, intehrated with the electronics that detect an preamplify the echoes. This circuit has a crystal local oscillator that allows precise measurement of time-lapsed between the emission of the signal and the recption of the different echoes of it.

The signal received is digitalised and processed by a DSP (Digital Sygnal Processor). The time measurements obtained thus are stored in an outgoing memory that can be read through a serial RS-232, RS-485 or Ethernet TCP/IP communication port, in the same manner as the discrete range measurement.

Figure 8:
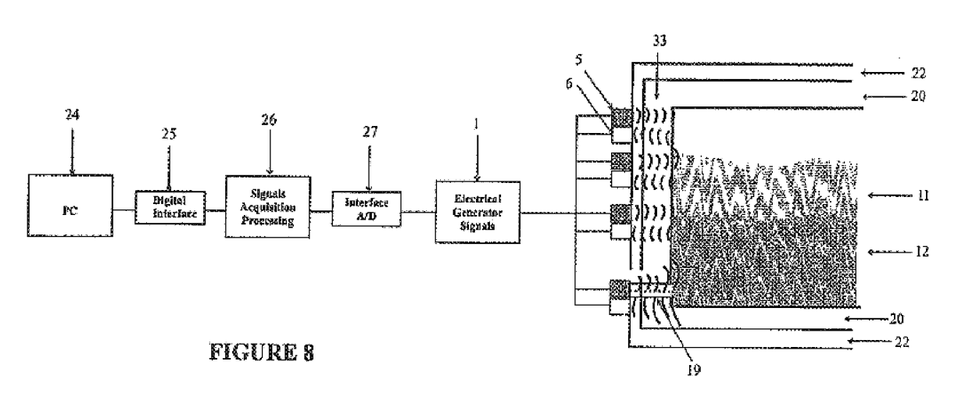
FIG. 8 presents a block diagram of the invention, showing the transducers with their respective sensors attached to the shell or mantle of the CT.

Likewise, if the on line temperature is known, corrective measures may be taken that contribute to a better operation of the CT. The avoidance of high fluctuations of temperature that provoke thermal shocks in the refractory allow to increase the CT operating time. As the mechanical waves are reflected with different amplitudes while crossing different media, these differences allow to directly relate the temperatures of the different media. Therefore, the unit that acquires and treats the signals (26), commands a power source (1) through an analogous/digital interface (27). The power source (1) controls a set of sonic transducers (5) attached to the shell (22) of a pirometallurgical converter (CT), by coupling pieces (21). The ultrasonic or sonic transducers (5), excited by the power source, emit mechanical waves (33) in the form of pulses that travel through the shell (22) and the refractory material (20). The mechanical waves (33) encounter the slag (11) or the metal bath (12), some are reflected and are received by sonic sensors (6), which in turn send analogous signals back to the power source. These signals are amplified and sent by means of an analogous/digital interface (27) from the power source to the unit that acquires and processes the signals (26), where they are processed and transformed in digital data sent to a computer (24) through a digital interface (25) between the computer (24) and the unit for acquisition and processing of signals (26). The data received by the computer can be observed through a procedure for displaying and monitoring said information.

The transducer of FIG. 3 can be mentioned as an example, operating at a frequency of 20 Khz. and a nominal power of 4 Kw, that applied to a situation like the one described in FIG. 7 allows to increase the reaction kinetics (34), detaching the copper entrapped (35) in the slag (11) and maintaining the air entrance (32) to the white metal (12) free of accretions (39). On the other hand, the greater quantity of chemical reactions that occur in the zone of direct application of ultrasonic waves will generate a higher concentration in the outgoing gases (sulphur dioxide) allowing in turn a better performance of the acid plant that receives those outgoing gases.

What we claim is:

1. A system arranged to be operable with a furnace having mixtures of materials exhibiting different phases, the system comprising:

a blowing tuyere generating an airflow, the tuyere having a furnace duct for transmitting the airflow to the furnace;

an electric signal generator for generating an electrical signal;

at least one transducer converting the electrical signal into mechanical waves, the mechanical waves travelling in the furnace duet together with the airflow in a wave direction which is transversal to the airflow direction along the furnace duct, the mechanical waves being transmitted to the furnace and being reflected by the materials according to their different phases to produce one or more reflected signals;

at least one sensor detecting the one or more reflected signals and generating a corresponding one or more detected signal; and a first processing element measuring a propagation time of the one or more reflected signals to determine the phase of the mixtures of materials through which the one or more reflected signals have propagated.

2. The system of claim 1, wherein the at least one transducer and the at least one sensor are placed on an external wall of the furnace.

3. The system of claim 1, further comprising
   a memory for storing values of the detected signals; and
   a display for showing the values.

4. The system of claim 1, wherein the at least one sensor is placed beside or integrated with the at least one transducer.

5. The system of claim 1, further comprising coupling means connecting the electric signal generator and the transducer with the furnace.

6. The system of claim 1, wherein the furnace is a converter.

7. The system of claim 6, wherein the converter is a Teniente Converter (CT).

8. The system of claim 1, wherein the furnace is a pyrometallurgical furnace.

9. The system of claim 1, further comprising:
   at least one amplifier, amplifying the one or more detected signal to form one or more amplified detected signals;
   an analog/digital interface digitizing the one or more amplified detected signals to form one or more digitized signals; and
   a data acquisition circuit acquiring the one or more digitized signals to form acquired data, the acquired data being processed by the processing element.

10. The system of claim 1, wherein the mixtures comprise a metal bath, a slag and gases.

11. The system of claim 1, wherein the mechanical waves are selected from the group consisting of sonic waves, ultrasonic waves and infrasonic waves.

12. The system of claim 1, wherein determination of a level of the phase of the mixtures is based on a corresponding level at which the at least one transducer is positioned.

13. A method for determining phases exhibited by mixtures of materials in a furnace, the method comprising:
    transmitting an airflow to the furnace in a duct along a first direction;
    generating an electrical signal;
    converting the electrical signal into mechanical waves;
    transmitting the mechanical waves in the duct together with the airflow along a second direction transversal to the first direction to the furnace, the mechanical waves being transmitted to the furnace and being reflected by the material according to their different phases to produce one or more reflected signals;
    detecting the one or more reflected signals and generating a corresponding one or more detected signal; and
    measuring a propagation time of the one or more reflected signal to determine the phase of the mixtures of material producing the one or more reflected signals.

14. The method of claim 13, wherein said mechanical waves are selected from the group consisting of sonic waves, ultrasonic waves and infrasonic waves.

15. The method of claim 13, wherein the furnace is a converter.

16. The method of claim 15, wherein the converter is a Teniente Converter (CT).

17. The method of claim 13, wherein the phases are a metal bath, a slag and gases.

* * * * *